United States Patent [19]

Taki et al.

[11] 4,397,951
[45] Aug. 9, 1983

[54] ELASTASE-CONTAINING COMPOSITION PERMITTING ELASTASE TO BE ABSORBED IN INCREASED AMOUNT

[75] Inventors: Kazuo Taki, Komae; Ryoichi Machida, Kashiwa; Kouichi Katayama, Tokyo, all of Japan

[73] Assignee: Eisai Co., Ltd., Japan

[21] Appl. No.: 343,333

[22] Filed: Jan. 27, 1982

[30] Foreign Application Priority Data

Feb. 3, 1981 [JP] Japan .................................. 56/13754

[51] Int. Cl.³ .......................... C12N 9/96; C12N 9/66; A61K 37/48
[52] U.S. Cl. .................................... 435/188; 435/218; 424/94
[58] Field of Search ................... 435/188, 218; 424/94

Primary Examiner—Lionel M. Shapiro
Attorney, Agent, or Firm—Wenderoth, Lind & Ponack

[57] ABSTRACT

An elastase-containing composition containing 0.5 to 50 parts by weight of sucrose fatty acid ester per part by weight of pure elastase, which composition permits elastase, useful as medicine for arterioscloerosis and hyperlipemia, to be absorbed in increased amount through intenstine.

7 Claims, 2 Drawing Figures

ELASTASE-CONTAINING COMPOSITION PERMITTING ELASTASE TO BE ABSORBED IN INCREASED AMOUNT

FIELD OF THE INVENTION

This invention relates to an elastase-containing composition which permits elastase to be absorbed in increased amount.

BACKGROUND OF THE INVENTION

Elastase is a decomposing enzyme for the water-soluble scleroprotein, elastin, and has been found to directly act on living body to normalize serum lipid level and increase elasticity of blood vessel. In particular, it is known that serum elastase level is low in patients suffering from arteriosclerosis and aged people and, in this point of view, elastase has recently attracted rapidly increasing attention as a medicine for arteriosclerosis and hyperlipemia.

However, absorption of elastase through intestine is extremely poor, because it is a polypeptide having a molecular weight of 25,900. For example, it is reported that, when 1 mg and 5 mg of $^{131}$I-elastase dissolved in a physiological saline solution were administered intraintestinally to rats, it was absorbed only 0.15% and 0.05%, respectively, even summing the amounts absorbed through blood vessel route and those through lymphatic vessel route. [Biochim. Biophys. Acta. 288 (1972), pp. 181–189]

That is, future medical application of elastase depends upon the development of means to increase the amount of elastase to be absorbed through intestine.

With this in mind, the inventors have made intensive investigations and, as a result, have found that addition of sucrose fatty acid ester remarkably increases absorption of elastase, thus having achieved the present invention.

SUMMARY OF THE INVENTION

The present invention is an elastase-containing composition containing 0.5 to 50 parts by weight of sucrose fatty acid ester per part by weight of pure elastase.

DETAILED DESCRIPTION OF THE INVENTION

Elastase is industrially extracted from porcine pancreas and is provided in a crude form including with other proteins or as pure elastase by further purification. Polysaccharides have been added thereto to stabilize elastase; for example, soluble dextran is compounded in a proportion of 50%. Elastase in the composition of the present invention may be in any form, and amounts of other ingredients than elastase can be determined based on the amount of pure elastase to be finally contained in the composition.

Sucrose fatty acid esters to be used in the present invention are commonly called sugar esters, and are nonionic surfactants produced by esterification between pure sucrose and pure fatty acid. Sucrose fatty acid esters are actually provided as mixtures of sucrose fatty acid monoester (mono-ester), sucrose fatty acid diester (di-ester), sucrose fatty acid triester (tri-ester), and higher ester(s), if any. Hydrophilicity of the ester increases as the content of mono-ester increases, whereas oleophilicity increases as the content of di-ester and/or tri-ester increases. In the present invention, sucrose fatty acid esters containing mono-ester in more amount tend to more increase absorption of elastase. More particularly, when the content of mono-ester is 50% or more, there results an increase in absorption of elastase, with the content of 70% or more being desirable.

The kind of fatty acid in the sucrose fatty acid ester is not particularly limited. Commercially available sucrose fatty acid esters are esters of fatty acids containing 12 to 18 carbon atoms, specifically, stearic acid, palmitic acid, lauric acid, and oleic acid. In the present invention, these commercially available ones may properly be used. There may be mentioned, for example, Ryoto Sugar Ester S-970, S-1170, S-1570, S-1670, P-1570, P-1670, SW-1570, PW-1570, LWA-1540, and OWA-1570 (made by Ryoto Co., Ltd.), which satisfy requirements for such sucrose fatty acid esters.

The sucrose fatty acid ester is compounded in an amount of 0.5 to 50 parts by weight per part by weight of pure elastase. If the content is less than the lower limit, there results only weak effect of increasing absorption of elastase whereas, if more than the upper limit, volume of the resulting composition becomes so much that it becomes difficult to be formed into a preparation.

In the present invention, the compounding ratio of pure elastase to sucrose fatty acid ester is specified in terms of weight ratio for convenience' sake. In fact, however, elastase content is indicated in terms of the elastase activity, and hence the compounding ratio can also be specified in terms of the part by weight of sucrose ester based on elastase activity. That is, at present available pure elastase has an activity of 340 elastase activity units (abbreviated as 340 EL. U) per mg measured by the method to be described hereinafter, and therefore the composition of the present invention is also defined as an elastase-containing composition containing 0.5 to 50 mg of sucrose fatty acid ester per 340 EL. U of elastase. More specifically, the composition of the present invention is an elastase-containing composition which contains 0.5 to 50 mg of sucrose fatty acid ester per 340 EL. U (measured by the measuring method described hereinafter) of elastase.

METHOD FOR MEASURING ELASTASE ACTIVITY

Figure 1:
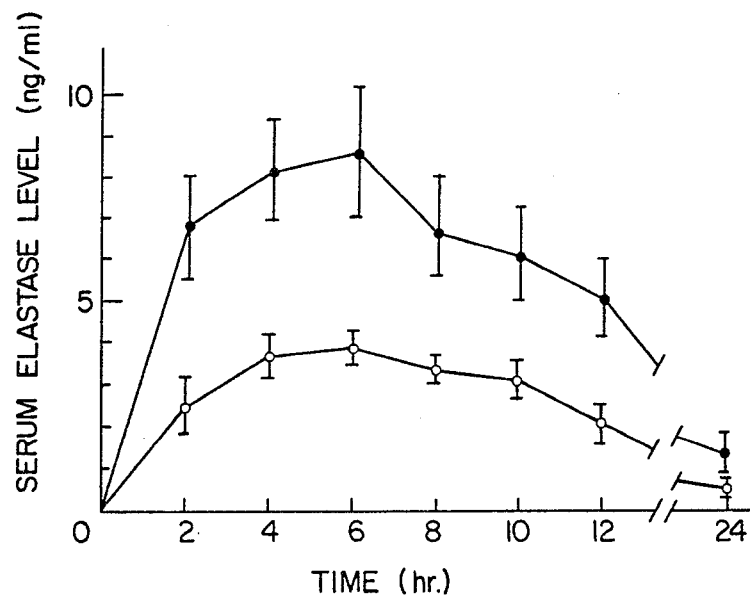
FIG. 1 shows serum elastase level curve in Wister strain rats.

An elastase-containing sample is accurately weighed, and dissolved in a diluted Palitzsch buffer solution to make a 250 ml elastase enzyme solution. 1 ml of the elastase enzyme solution is added to 4 ml of a substrate solution, and incubation is conducted for 30 minutes at 37°±0.1° C. with shaking at 100 strokes/min. Then, 5 ml of a reaction-terminating solution is added thereto and, after shaking for 10 minutes at 37°±0.1° C., the solution is centrifuged for 10 minutes at 3,000 to 3,500 rpm. The resulting supernatant is used as a sample solution.

Apart from the above, 4 ml of a substrate solution, 5 ml of a reaction-terminating solution, and 1 ml of an elastase enzyme solution are taken up in this order, and the resulting mixture is shaked for 40 minutes at 37°±0.1° C., followed by centrifugation for 10 minutes at 3,000 to 3,500 rpm. The supernatant thus obtained is used as a blank test solution.

Absorbances at 275 mμ of the sample solution and the blank test solution are measured with water as a reference. The amount of soluble elastin produced per minute as a result of decomposition of insoluble elastin under the above-described measuring conditions is determined as an amount of tyrosine (μg) by which EL. U is indicated.

The above-referred diluted Palitzsch buffer solution is prepared by mixing 1000 ml of an aqueous solution containing 19.10 g of borax dissolved therein with 1000 ml of an aqueous solution containing 12.40 g of boric acid and 2.92 g of sodium chloride dissolved therein, adjusting pH to 8.8, and adding 100 ml of water to 100 ml of the resulting solution.

The substrate solution is prepared by adding a diluted Palitzsch buffer solution to 0.30 g of elastin (made by ICN Pharmaceuticals Co.) to make a 50 ml solution. This solution is used after allowing to stand for 30 minutes.

The reaction-terminating solution is prepared by adding water to 1.0 g of sodium dodecylsulfate to make a 100 ml solution, followed by adding a 0.5 M acetic acid-sodium acetate buffer solution (pH 5.3) to 5 ml of the resulting solution to make a 100 ml solution.

The dosage form of the composition of the present invention may be any of orally administerable ones. However, since elastase is unstable to gastric acid, the dosage form is desirably a gastric acid-resistant form, for example, enteric granules, enteric tablets, and hard capsules filled with enteric granules. These forms may be produced in a conventional manner using proper excipients. In addition, the composition of the present invention may be prepared in a powdery or granular form, which is filled in enteric hard capsules.

The effects of the present invention will be described by reference to the following effect examples.

EFFECT EXAMPLE 1

Samples 2 ml of distilled water was added to a predetermined amount of sucrose fatty acid ester to well emulsify. Upon use, there are added to the emulsion 3 mg of pure elastase (1020 EL. U) and the amount of sodium chloride necessary to make isotonic, followed by mixing in a thermomixer to prepare a uniform solution, which was used as a sample. As a control, there was used a solution prepared by dissolving 3 mg of pure elastase (1020 EL. U) in a physiological saline solution. Sucrose fatty acid esters used are tabulated in Table 1 wherein ester composition of the respective sucrose fatty acid esters and kind and ratio of fatty acid are given as well.

TABLE 1

| Sucrose Fatty Acid Ester | Ester Composition | | Fatty Acid Component | |
|---|---|---|---|---|
| | Mono-ester | Di-ester Tri-ester | Stearic Acid | Palmitic Acid |
| S-370 | 20 | 80 | 70 | 30 |
| S-970 | 50 | 50 | 70 | 30 |
| S-1570 | 70 | 30 | 70 | 30 |
| S-1670 | 75 | 25 | 70 | 30 |
| P-1570 | 70 | 30 | 30 | 70 |
| LWA-1540 | 70 | 30 | Lauric Acid | 50 |
| OWA-1570 | 70 | 30 | Oleic Acid | 70 |

In the above table, the column of "Sucrose Fatty Acid Ester" indicates product No. of Ryoto Sugar Ester (made by Ryoto Co., Ltd.), and each numerical value, for example, 20 indicates about 20%.

Method

Wister strain male rats (weighing 280 to 340 g) were fasted for 24 hours, and the abdomen was cut open along the median line under anesthesia with ether. Then, each of the above-described samples was introduced into the upper portion of duodendum, followed by suturing. Subsequently, the rats were left with free access to water, and blood was taken through carotid at predetermined time intervals. The blood samples were centrifuged to obtain serum. Serum elastase levels were measured according to the following enzyme-immunological method.

Enzyme-immunological method 0.45 ml of buffer solution G and IgG-silicon piece (corresponding to 0.5 μg of IgG) were added to 50 μl of serum. The resulting mixture was incubated for 4 hours at 37° C., and allowed to stand overnight at 4° C. The solution was washed once with 1 ml of buffer solution G, then twice with buffer solution A. 0.05 ml of buffer solution A and 0.1 ml of IgG-galactosidase (1750μ units) were added thereto, and incubation was conducted at 37° C. for 5 hours. The solution was then washed twice with 1 ml of buffer solution A, transferred to a new test tube, and 0.05 ml of buffer solution A and 0.1 ml of $1.5 \times 10^{-4}$ M 4-methylumbelliferyl β-D-galactoside were added thereto, followed by incubation at 37° C. for 10 minutes. Then, 2.5 ml of a 0.1 M glycine-sodium hydroxide solution (pH 10.3) was added thereto to terminate the reaction. Fluorescence intensities at an exciting wave-length of 360 nm and at a fluorescence wave-length of 450 nm were measured, respectively.

The above-mentioned buffer solution G is a 0.01 M phosphate buffer solution (pH 7.0) containing 0.3 M NaCl, 1 mM $MgCl_2$, 0.1% bovine serum albumin, 0.1% $NaN_3$ and 0.5% gelatin, and the buffer solution A is a 0.01 M phosphate buffer solution (pH 7.0) containing 0.1 M NaCl, 1 mM $MgCl_2$, 0.1% bovine serum albumin, and 0.1% $NaN_3$.

Results

With each sample, serum elastase level was plotted versus time to determine elastase AUC (area under the curve of serum elastase levels) from an administration to 24 hours thereafter. Table 2 shows the results thus obtained.

In the Table, AUC of each sample is given as a relative ratio, taking AUC of sucrose fatty acid ester-free sample as 1.0.

TABLE 2

| Sucrose Fatty Acid Ester | | | |
|---|---|---|---|
| Kind | Compounding Ratio | AUC | Relative Ratio |
| — | — | 50.2 ± 7.78 | 1.0 |
| S-370 | 4 | 45.2 ± 16.9 | 0.9 |
| S-970 | 4 | 65.3 ± 1.88 | 1.3 |
| S-1570 | 4 | 136 ± 20.1 | 2.7 |
| P-1570 | 0.5 | 56.5 ± 15.4 | 1.1 |
| P-1570 | 1 | 70.3 ± 8.9 | 1.4 |
| P-1570 | 2 | 117 ± 20.6 | 2.3 |
| P-1570 | 4 | 161 ± 17.8 | 3.2 |
| P-1670 | 4 | 151 ± 14.0 | 3.0 |
| LWA-1540 | 4 | 110 ± 6.87 | 2.2 |
| OWA-1540 | 4 | 100 ± 8.55 | 2.0 |

In the above table, the compounding ratios are indicated in terms of parts by weight of sucrose fatty acid ester per part by weight of pure elastase.

As is seen from Table 2, the sucrose fatty acid esters of the present invention are effective, when 50% or more of the ester is sucrose fatty acid mono-ester; and the lower limit of the ester content per part of pure elastase is 0.5 part by weight.

EFFECT EXAMPLE 2

Samples

Compositions having the following formulations were directly tableted to prepare mini-tablets of 4 mm in diameter and 40 mg in weight, which were used as samples. In the formulation, Ryoto Sugar Ester P-1570 is the same as described in Effect Example 1, Table 1.

Formulation

| Elastase (85 EL. U/mg) | 12 | 12 |
| Ryoto Sugar Ester P-1570 | — | 40 |
| Spray-dried lactose | 40 | 40 |
| Crystalline cellulose | 43 | 43 |
| CMC calcium | 25 | 25 |

Numerical values indicate weight ratios in the formulations.

Method

Wister strain male rats (weighing 280 g to 340 g) were fasted for 24 hours. The abdomen was cut open along the median line under anesthesia with ether. Mini-tablets were cut into accurately equal four pieces, and the tablets were inserted into duodendum through glass funnel in an amount corresponding to 12 mg of elastase. A silicon tube (3 mm in inside diameter, 5 mm in outside diameter, and 8 mm in length) was inserted into intestine, and the median line was sutured. Subsequent procedures were conducted in the same manner as in Effect Example 1 to take blood and measure serum elastase level.

Results

Serum elastase level curve is shown in FIG. 1. FIG. 1 is a graph showing an elastase level curve in blood serum obtained in experiments in Effect Example 2, wherein —●—●— represents the curve obtained by using Ryoto Sugar Ester P-1570-containing mini-tablets, and —○—○— represents that obtained by using mini-tablets containing no such sucrose ester.

Table 3 shows elastase AUC from administration to 24 hours thereafter. In the Table, AUC values are given as relative ratios, taking AUC of sucrose fatty acid ester-free sample as 1.0.

TABLE 3

| Sucrose Fatty Acid Ester | | | Relative |
| Kind | Compounding Ratio | AUC | Ratio |
| --- | --- | --- | --- |
| — | — | 49.8 ± 6.13 | 1.0 |
| P-1570 | 13 | 117 ± 17.2 | 2.3 |

In Table 3, the compounding ratios are indicated in terms of parts by weight of sucrose fatty acid ester per parts by weight of pure elastase.

It is seen from Table 3 that the composition of the present invention is also effective in the form of tablets.

EFFECT EXAMPLE 3

Sample

An aqueous sample solution for test was prepared by adding 55.2 mg of elastase (326 EL. U/mg) and 736.2 mg of Ryoto sucrose fatty acid ester (P-1570) to 5 ml of water. An aqueous control solution was prepared by adding 55.2 mg of elastase (326 EL. U/mg) alone to 5 ml of water.

Method

Four beagles (weighing 10.5–14.0 kg) were divided into 2 aliquot groups, each being 2 subjects. Cross-over method was twice applied to the subjects, using the aqueous sample solution and the aqueous control solution. The subjects were fasted overnight, and the abdomen was cut open along the median line under anesthesia in the following morning. Then, 5 ml of the respective sample and control solutions were introduced into duodendum using injection tube, followed by immediate suturing. 3 ml of the blood were respectively taken prior to the administration of the solutions, and at the elapsed times of 1, 2, 4, 6, 8, 10, 12 and 24 hours after the administration of the solutions. About 1 ml of serum was respectively separated by means of centrifuge.

Serum elastase levels were measured in accordance with "Enzyme-immunological method", as described in the effect example 1.

Results

Figure 2:
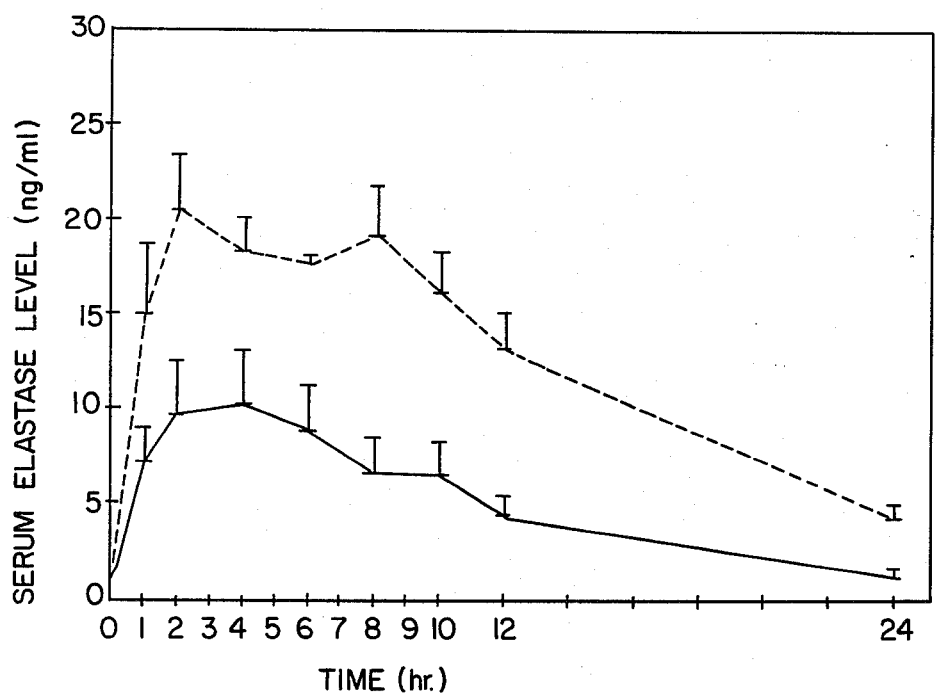
FIG. 2 shows serum elastase level curve in beagles.

Serum elastase level curve is shown in FIG. 2, wherein the actual curve shows an elastase level in blood serum obtained by the use of the aqueous control solution, and the dotted line curve shows the level obtained by the use of the aqueous sample solution.

From FIG. 2, it is apparent that, with reference to the elastase levels in blood serum at the respectively taken times, all levels of the sample solution are higher than those of the control solution.

Table 4 shows the prameters, that is, the necessary time for reaching to the maximum level in serum ($T_{max}$), the maximum level in serum ($C_{max}$), and elastase AUC from administration to 24 hours thereafter. In the Table, the AUC value in the control solution is taken as 1.0, and the relative ratios are given in the Table.

From the Table 4, it is clear that no difference is found in $T_{max}$; $C_{max}$ of the sample solution is 2.32 times higher than that of the control solution; and AUC value of the sample solution is 2.44 times higher than that of the control solution.

TABLE 4

| Sample | $T_{max}$ (hr) | $C_{max}$ (ng/ml) | $AUC_{0-24hr}$ (ng.hr/ml) | Relative Ratio |
| --- | --- | --- | --- | --- |
| Control Solution | 3.75 ±0.25 | 10.27 ±2.76 | 125.84 ±32.84 | 1.0 |
| Control Solution | 5.00 ±1.29 | 23.92 ±2.18 | 307.18 ±20.24 | 2.4 |

The present invention will now be described in more detail by reference to examples of preferred embodiments of the present invention which, however, are not to be construed as limiting the present invention in any way.

EXAMPLE 1

100 g of elastase (85 EL. U/mg) and 400 g of Ryoto Sugar Ester P-1540 were slightly ground to prepare homogeneous powder. To this powder were added 500 g of spray-dried lactose, 495 g of crystalline cellulose, and 300 g of CMC calcium, and the whole was mixed. Then, 5 g of calcium stearate was dusted over the mixture through a 50-mesh sieve, and the whole was uniformly mixed, followed by tableting to form tablets of 8 mm in diameter and 180 mg in weight. A solution of the following formulation was spray-coated on the tablets to produce 200 mg enteric tablets.

Formulation

| Eudragit L | 5 parts |
|---|---|
| Triacetin | 1 part |
| Ethanol | 94 parts |

EXAMPLE 2

| Non-paril seeds | 2.5 kg |
|---|---|
| HPC-L | 0.5 kg |
| Ethanol | proper amount |
| Elastase (85 EL. U/mg) | 0.6 kg |
| Ryoto Sugar Ester P-1570 | 1.5 kg |
| Corn Starch | 2.7 kg |
| HP-55 | 1.95 kg |
| Myvacet 9-40 | 0.25 kg |
| Ethanol | proper amount |

Non-paril seeds were loaded in a centrifugal-fluidized-coating apparatus. A mixed powder composed of elastase, Ryoto Sugar Ester, and corn starch was dusted thereover after spraying an ethanol solution of HPC-L to form granules. An ethanol solution of Myvacet 9-40 and HP-55 was spray-coated on the thus formed granules using the same apparatus to form enteric granules.

The above-mentioned Non-paril seeds are a mixture of sucrose and corn starch; HPC-L is hydroxypropyl cellulose; HP-55 is hydroxypropyl methyl cellulose phthalate; and Myvacet 9-40 is acetyl monoglyceride.

EXAMPLE 3

Enteric granules obtained in Example 2 were filled in #3 hard capsules in an amount of 200 mg in each capsule to form hard capsule preparation.

EXAMPLE 4

| Elastase (340 EL. U/mg) | 0.2 kg |
|---|---|
| DK ester SS | 1.2 kg |
| Sugar powder | 8.5 kg |
| Corn starch | 1.8 kg |
| Ethyl cellulose | 0.1 kg |
| Polyethylene glycol 6000 | 1.0 kg |
| Hydrogenated castor oil | 0.2 kg |

-continued

| Trichloroethane | proper amount |
|---|---|

A mixture of elastase, DK ester SS, sugar powder and corn starch is kneaded with trichloroethane solution which contains ethyl cellulose and polyethylene glycol 6000. The resulting mixture was granulated by the use of screen having 0.7 mm meshes. After the granules were dried at 40° C., hydrogenated castor oil was sprayed through 80 mesh sieve. The whole was thoroughly mixed, and compressed to produce tablets, each of which having a diameter of 7 mm and weighing 130 mg. To the tablets were spray-coated the solution as described in Example 1, to produce enteric tablets weighing 145 mg.

The above-mentioned "DK ester SS" is trade name of sucrose fatty acid ester which was produced and sold by Dai-ichi Kogyo Seiyaku Co., Ltd. in Japan and contains 95% of sucrose fatty acid mono-ester.

The invention has been described in detail with particular reference to certain preferred embodiments thereof, but it will be understood that variations and modifications can be effected within the spirit and scope of the invention.

What is claimed is:

1. An elastase-containing composition containing 0.5 to 50 parts by weight of sucrose fatty acid ester per part by weight of pure elastase.

2. The elastase-containing composition as claimed in claim 1, wherein said sucrose fatty acid ester is a mixture of sucrose fatty acid mono-ester, sucrose fatty acid di-ester, and sucrose fatty acid tri-ester.

3. The elastase-containing composition as claimed in claim 2, wherein said sucrose fatty acid ester mixture contains 50% or more sucrose fatty acid mono-ester.

4. The elastase-containing composition as claimed in claim 3, wherein said sucrose fatty acid ester mixture contains 70% or more sucrose fatty acid mono-ester.

5. The elastase-containing composition as claimed in claim 1, 2, 3 or 4, wherein said sucrose fatty acid ester is an ester between fatty acid containing 12 to 18 carbon atoms and sucrose.

6. The elastase-containing composition as claimed in claim 1, 2, 3, or 4, wherein said fatty acid is selected from the group consisting of stearic acid, palmitic acid, lauric acid, and oleic acid.

7. The elastase-containing composition as claimed in claim 5, wherein said fatty acid is selected from the group consisting of stearic acid, palmitic acid, lauric acid, and oleic acid.

* * * * *